United States Patent [19]

Shinmen et al.

[11] Patent Number: 5,116,751
[45] Date of Patent: May 26, 1992

[54] PROCESS FOR PRODUCING PEROXIDASE

[75] Inventors: Yoshifumi Shinmen, Kyoto; Sumio Asami; Norihide Amano, both of Osaka; Teruo Amachi, Hyogo; Hajime Yoshizumi, Osaka, all of Japan

[73] Assignee: Suntory Limited, Osaka, Japan

[21] Appl. No.: 643,166

[22] Filed: Jan. 22, 1991

Related U.S. Application Data

[63] Continuation of Ser. No. 377,759, Jul. 10, 1989, abandoned, which is a continuation of Ser. No. 91,342, Aug. 11, 1987, abandoned, which is a continuation of Ser. No. 791,439, Oct. 25, 1985, abandoned.

[30] Foreign Application Priority Data

Oct. 26, 1984 [JP] Japan .................. 59-225485

[51] Int. Cl.$^5$ ............................. C12N 9/08
[52] U.S. Cl. .................... 435/194; 435/154; 435/911
[58] Field of Search .............. 435/192, 154, 911

[56] References Cited

U.S. PATENT DOCUMENTS 4,328,312 5/1982 Tsurumi et al. .................. 435/192

FOREIGN PATENT DOCUMENTS 0200565 11/1986 European Pat. Off. .
57-99192 6/1982 Japan .................. 435/192
59-179075 10/1984 Japan .................. 435/192
2167421 5/1986 United Kingdom .

OTHER PUBLICATIONS

Patent Abstracts of Japan, vol. 6, No. 186 (C-126)(1064) 1982.
Patent Abstracts of Japan, vol. 9, No. 32 (C-265) (1255), 1985.
ATCC Catalogue of Fungi/Yeasts 16th Edition, 1984, pp. 92-95.
Phillip E. Reynolds et al., American Journal of Botany, 60(4 suppl), (1973), p. 26.
European Search Report, date Jun. 15, 1987.
J. Gen. Appl. Microbiol., 26, 229-238 (1980), "Effect of 2-Deoxy-D-Glucose on the Induction of Tyrosinase in Coprinus Macrorhizus", (Nyunoya et al.).
Supplement to Transactions of the British Mycological Society, New Check List of British Agarics and Boleti, R. W. G. Dennis and P. D. Orton and F. B. Hora, Jun. 1960.

Primary Examiner—Charles L. Patterson
Attorney, Agent, or Firm—Cushman, Darby & Cushman

[57] ABSTRACT

A novel peroxidase was obtained from a fast growing microorganism of the genus Coprinus cinereus. The fungal peroxidase is comparable to the conventional peroxidase derived from horseradish or Japanese radish in that it can be used either as a clinical or diagnostic reagent or as a marker enzyme in enzyme immunoassay.

5 Claims, 1 Drawing Sheet

PROCESS FOR PRODUCING PEROXIDASE

This is a continuation of application Ser. No. 07/377,759, filed on Jul. 10, 1989, which was abandoned upon the filing hereof which is a continuation of 091,342, filed Aug. 31, 1987 which is a continuation of 791,439 filed Oct. 25, 1985, now abandoned.

BACKGROUND OF THE INVENTION

1. Field of the Invention

The present invention relates to a process for producing a peroxidase using a microorganism. More particularly, the invention relates to a process for producing a peroxidase that is produced by a fungi of the genus Coprinus of the basidiomycetes and which develops color with the aid of a hydrogen donor such as a 4-amino-antipyrine (hereunder abbreviated as 4-AA)-phenol system, a 3-methyl-2-benzothiazolinone hydrazone (hereunder MBTH)-diethylaniline (hereunder DEA) system, and a 2,2'-azino-di(3-ethylbenzothiazoline)-6-sulfonic acid (hereunder ABTS).

2. Prior Art

Peroxidase is an enzyme that oxidizes a variety of compounds in the presence of hydrogen peroxide. Currently, peroxidase is used as a clinical or diagnostic reagent in combination with a variety of oxidases for the assay of glucose, cholesterol, phospholipids and uric acid. Another current use of peroxidase is as a marker enzyme in enzyme immunoassay. The only commercially available sources of peroxidase are plants such as horseradish and Japanese radish. Since the peroxidase originating from such plants contains isozymes of slightly different properties, they must be separated laboriously in order to obtain a pure form of peroxidase suitable for use as a diagnostic reagent.

Peroxidases originating from microorganisms are also known and they include Cytochrome C peroxidase and NADH peroxidase produced from bacteria and fungi. However, these peroxidases are not non-specific as are the ordinary peroxidases derived from horseradish and Japanese radish, and such peroxidases specific to a particular system are not suitable for use as clinical and diagnostic reagents. It has recently been reported that peroxidase using o-dianisidine as a hydrogen donor can be produced from *E. coli* or microorganisms of the genus Myrothecium. However, this peroxidase is also unsuitable as a diagnostic reagent since the use of o-dianisidine in clinical and diagnostic agents is increasingly discouraged because of its potential carcinogenic effects.

SUMMARY OF THE INVENTION

The present inventors made various efforts to obtain from fast growing microorganisms a peroxidase that is comparable to the conventional peroxidase derived from horseradish or Japanese radish in that it can be used either as a clinical or diagnostic reagent or as a marker enzyme in enzyme immunoassay. To attain this object, the inventors isolated a large number of naturally occurring microorganisms and examined their ability to produce peroxidase that develops color with the aid of a hydrogen donor such as a 4-AA-phenol system, MBTH-DEA system or ABTS. As a result, the inventors found a fungal strain of the genus Coprinus that is capable of producing a peroxidase in a high yield. The present invention has been accomplished on the basis of this finding.

DETAILED DESCRIPTION OF THE INVENTION

Figure 1:
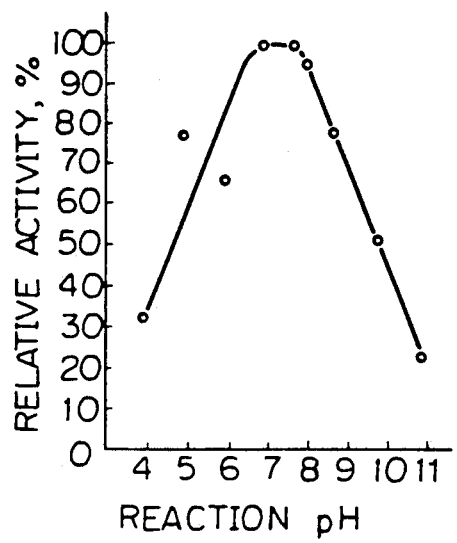
FIG. 1 is a graph showing the relationship between the reaction pH and the relative activity of the peroxidase of the present invention.

Examples of microorganisms of the genus Coprinus that have the ability to produce peroxidase include *Coprinus cinereus* f. microsporus IFO 8371, *C. cinereus* IFO 30114, *C. cinereus* IFO 30627, *C. cinereus* IFO 30628 and *C. cinereus* IFO 31333, all being stored at the Institute for Fermentation, Osaka, Japan.

The strain used in the present invention may be cultured by inoculating a liquid or solid medium with spores or mycelia from the strain or a liquid seed culture obtained by precultivation. A liquid medium may contain any common carbon sources such as glucose, fructose, xylose, saccharose, maltose, soluble starch, molasses, glycerol and mannitol. Usable nitrogen sources include naturally occurring substances such as peptone, yeast extract, malt extract, meat extract, casamino acids, and corn steep liquor, as well as organics such as urea, and inorganics such as sodium nitrate and ammonium nitrate. Inorganic salts (e.g. phosphates, magnesium sulfate, iron sulfate and copper sulfate) and vitamins may optionally be used as trace nutrient sources. Any of these components may be incorporated in a medium in any concentration that will not be detrimental to the growth of the microorganism of interest. For practical purposes, carbon sources are generally used in concentrations ranging from 0.1 to 10 wt%, preferably from 1 to 5 wt%, while nitrogen sources are in the range of 0.01 to 5 wt%, preferably 0.1 to 2 wt%. The cultivation temperature ranges from 10° to 42° C., preferably from 30° to 37° C. The medium is adjusted to a pH value in the range of 4-10, preferably 6-9, and cultivation is conducted by agitation culture under aeration, shake culture or stationary culture, for a period which generally lasts 3 to 14 days.

A solid medium may be prepared from wheat bran, rice hulls, rice bran or any other suitable materials that are mixed with 50-100 wt% of water. Cultivation is carried out at temperatures between 10° and 42° C., preferably between 30° and 37° C., for a period of 3-14 days. If necessary, the medium may be supplemented with suitable nitrogen sources, inorganic salts or trace nutrient sources. For mass cultivation, a liquid medium is preferred.

The culture obtained by the procedures described above has peroxidase accumulated therein. The term "culture" used here means either the cultured cells, the culture supernatant, the mixture thereof, or a culture filtrate if a liquid medium is used; if a solid medium is used, the term "culture" means the mixture of the cells and the medium on which they have grown.

For example, if a liquid medium is used, peroxidase may be recovered from the culture mixture by the following procedures. When the full growth of the organism is attained, the culture mixture is subjected to a suitable solid-liquid separation means such as centrifugation or filtration, so as to obtain a crude enzyme solution free from the cells and insoluble matter. Peroxidase in the cells may be extracted by disrupting them by a suitable method such as grinding or ultrasonic treatment. Cells may be directly subjected to an ultrasonic treatment in a culture medium so as to disrupt the cells and a crude enzyme solution may be obtained by removing any insoluble matter from the treated solution.

If cultivation is performed on a solid medium, a crude enzyme solution may be obtained by the following procedures: water is added to the solid medium containing the cultured cells, and any insoluble matter is removed from the mixture either immediately or after disrupting the cells by a suitable means such as ultrasonic treatment.

A pure form of peroxidase may be isolated from the crude enzyme solution by conventional enzyme purification techniques, such as organic solvent fractionation, ammonium sulfate fractionation, dialysis, isoelectric precipitation and column chromatography, which may be used either independently or in combination.

The activity of the peroxidase in accordance with the present invention may be determined by the following method, wherein a 4-AA-phenol system, for example, is used as a hydrogen donor. First, 1.3 ml of 0.1% phenol solution, 0.25 ml of 0.2% 4-AA solution and 0.2 ml of 0.02% hydrogen peroxide solution are added to 1 ml of 0.1 M phosphate buffer (pH, 7.0) and the mixture is prewarmed to 37° C. To the prewarmed mixture, 0.25 ml of a specific enzyme solution is added and subjected to reaction for 10 minutes. After the reaction, 0.2 ml of 20% sodium azide solution is added and the absorbance of the mixture is measured at 500 nm to obtain a reaction value, which is compared with a control value obtained by the same procedure except that the hydrogen peroxide solution is replaced by an equal volume (0.2 ml) of water. One unit (U) of peroxidase activity is indicated as the amount of oxygen that oxidizes 1 micromole of 4-AA-phenol per minute. The activity (U/ml) of peroxidase in an enzyme solution or culture solution is determined by the formula: $0.198 \times O.D._{500} \times$ (the dilution rate of the enzyme or culture solution), wherein $O.D._{500}$ is the absorbance value after subtracting the control value.

The peroxidase obtained by the present invention has the following properties.

(1) Enzyme action

The peroxidase in accordance with the present invention catalyzes the oxidation of various compounds in the presence of hydrogen peroxide by the mechanism shown below:

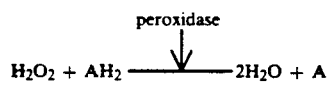

$$H_2O_2 + AH_2 \xrightarrow{\text{peroxidase}} 2H_2O + A$$

(wherein $AH_2$ is a hydrogen donor, and A is an oxidized hydrogen donor).

(2) Specificity for hydrogen donor

The specificity of the peroxidase for a variety of hydrogen donors is shown in Table 1.

TABLE 1

| H₂ donor | Activity | H₂ donor | Activity |
|---|---|---|---|
| Phenol | +++ | Hydroquinone | + |
| Pyrogallol | +++ | p-hydroxybenzoic acid | ++ |
| p-anisidine | ++ | p-aminobenzoic acid | + |

TABLE 1-continued

| H₂ donor | Activity | H₂ donor | Activity |
|---|---|---|---|
| o-dianisidine | +++ | ABTS | +++ |
| Guaiacol | ++ | Diethylaniline | ± |

(3) Optimum pH

The optimum pH range at which the peroxidase exhibits the highest activity was checked by using samples having the same formulation as used for the assay of peroxidase activity in above (1), except that different buffers were used for different pH ranges: 0.1 M acetate buffer for pH 3.5–5.5, 0.1 M phosphate buffer for pH 5.5–8.0, 0.1 M tris-HCl buffer for pH 7.5–9.0, and 0.1 M glycine-sodium hydroxide buffer for pH 8.5–9.0. The results are summarized in FIG. 1.

(4) Optimum working temperature

Figure 2:
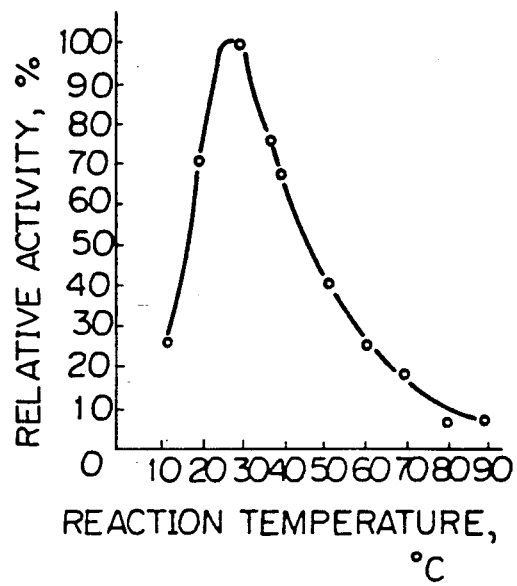
FIG. 2 is a graph showing the relationship between the reaction temperature and the relative activity of the peroxidase.

The activity of the peroxidase was measured over the temperature range of 10°–90° C., and the results are shown in FIG. 2.

(5) pH stability

Figure 3:
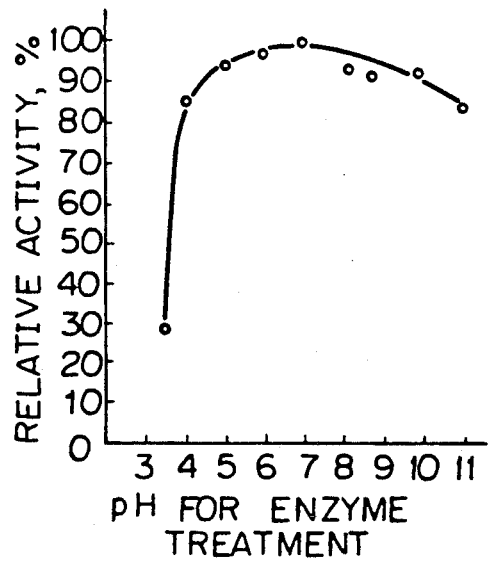
FIG. 3 is a graph showing the pH stability of the peroxidase.

Different buffers were used for different pH ranges: 0.1 M acetate buffer for pH 3.5–5.0, 0.1 M phosphate buffer for pH 6.0–8.0, 0.1 M tris-HCl buffer for pH 8.0–9.0, and 0.1 M glycine-NaOH buffer for pH 9.0–12.0. To 0.9 ml of a specific buffer solution was added 0.1 ml of the peroxidase solution and the mixture was left to stand at 30° C. for 16 hours. The so treated enzyme solution was diluted 10-fold with 0.02M phosphate buffer (pH, 7.0) and the activity of the enzyme was measured. The results are shown in FIG. 3.

(6) Temperature stability

Figure 4:
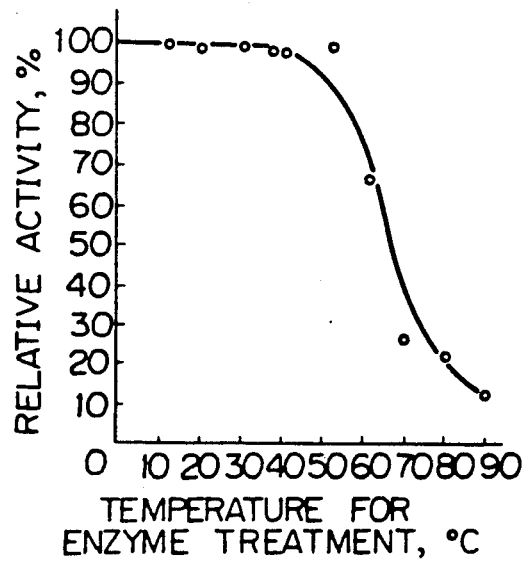
FIG. 4 is a graph showing the temperature stability of the peroxidase.

Samples each prepared by adding 0.1 ml of the enzyme solution to 1.9 ml of 0.02M phosphate buffer (pH, 7.0) were held at varying temperature (10°–90° C.) for 30 minutes. Immediately thereafter, the samples were cooled with iced water for 10 minutes and the residual enzyme activity in each sample was measured. The results are shown in FIG. 4.

The following Examples are provided for further illustration of the invention.

EXAMPLE 1

Ten milliliters of a medium (pH, 6.0) containing 1% glucose, 0.5% polypeptone, and 0.3% yeast extract was put into a test tube having a diameter of 24 mm, and sterilized at 120° C. for 15 minutes. The sterilized medium was inoculated with a platinum loop of Coprinus cinereus IFO 8371, with a platinum loop of *Coprinus cinereus* f. microsparsus IFO 8371, which was shake-cultured on a recipro-shaker (300 rpm) at 30° C. for 6 days. The culture mixture was filtered and the titer of peroxidase in the filtrate was found to be 1.3 U/ml.

EXAMPLE 2

*Coprinus cinereus* IFO 30627 was cultured for 7 days as in Example 1 and the filtrate of the culture had a peroxidase activity of 3.4 U/ml.

EXAMPLE 3

A medium (100 ml) of the same composition as that used in Example 1 was charged into a 500-ml Erlenmeyer flask and sterilized at 120° C. for 20 minutes. The sterilized medium was inoculated with a platinum loop of *Coprinus cinereus* IFO 30628 and shake-cultured on a recipro-shaker (110 rpm) at 34° C. for 6 days. The culture mixture was filtered and the titer of peroxidase in the filtrate was found to be 1.7 U/ml.

What is claimed is:

1. A process for producing a peroxidase comprising culturing a peroxidase-producing microorganism which is selected from the group consisting of *Coprinus cinereus* f. microsporous IFO 8371, *Coprinus cinereus* IFO 30114, *Coprinus cinereus* IFO 30627, *Coprinus cinereus* IFO 30628 and *Coprinus cinereus* IFO 31333 in a liquid medium and recovering the peroxidase secreted into the liquid medium.

2. A process for producing a peroxidase comprising culturing a peroxidase-producing microorganism which is selected from the group consisting of *Coprinus cinereus* f. microsporous IFO 8371, *Coprinus cinereus* IFO 30114, *Coprinus cinereus* IFO 30627, *Coprinus cinereus* IFO 30628 an d*Coprinus cinereus* IFO 31333 in a solid medium and recovering the peroxidase secreted into the solid medium.

3. A process according to claim 1, wherein the culture medium contains 0.1 to 10 wt % of carbon sources selected from the group consisting of glucose, fructose, xylose, saccharose, maltose, soluble starch, molasses, glycerol and mannitol; 0.01 to 5 wt % of nitrogen sources selected from the group consisting of peptone, yeast extract, malt extract, means extract, casamino acids, corn steep liquor, urea, sodium nitrate and ammonium nitrate; and a growth supporting amount of inorganic salts selected from the group consisting of phosphate, magnesium sulfate, iron sulfate and copper sulfate.

4. A process according to claim 1, wherein the culture is carried out at a temperature of between 10° to 42° C. and at a pH between 4 and 10 for 3 to 14 days.

5. A process according to claim 4, wherein the peroxidase produced by said process does not contain isozymes.

* * * * *